United States Patent
Kurochi

(10) Patent No.: US 8,126,119 B2
(45) Date of Patent: Feb. 28, 2012

(54) COLLIMATOR UNIT, RADIATION DETECTING DEVICE, AND RADIODIAGNOSTIC SYSTEM

(75) Inventor: Haruo Kurochi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 193 days.

(21) Appl. No.: 12/727,840

(22) Filed: Mar. 19, 2010

(65) Prior Publication Data

US 2010/0239072 A1    Sep. 23, 2010

(30) Foreign Application Priority Data

Mar. 19, 2009  (JP) ................................ 2009-067200

(51) Int. Cl.
    *G21K 1/02*   (2006.01)
(52) U.S. Cl. ......................................... 378/147; 378/19
(58) Field of Classification Search ................ 378/4, 19, 378/147–149, 154
    See application file for complete search history.

(56) References Cited

U.S. PATENT DOCUMENTS

| 4,768,765 A | 9/1988 | Kurochi ....................... 269/296 |
| 7,526,875 B2 | 5/2009 | Freund ............................ 33/645 |
| 7,612,343 B2 | 11/2009 | Vickers ...................... 250/363.1 |
| 2009/0225955 A1 | 9/2009 | Igarashi et al. |
| 2010/0014642 A1 | 1/2010 | Halazonetis et al. |

FOREIGN PATENT DOCUMENTS

| JP | 2001-174566 | 6/2001 |
| JP | 2003-207575 | 7/2003 |

*Primary Examiner* — Courtney Thomas
(74) *Attorney, Agent, or Firm* — Armstrong Teasdale LLP

(57) ABSTRACT

A pair of holding plates formed with a plurality of grooves each wider than the thickness of each collimator plate are disposed in parallel so that the respective surfaces formed with the grooves confront each other. Urging members are disposed on the holding members. When the urging members slide in the arranged direction of the grooves along the grooves-formed surfaces of the holding members, the urging members urge individual collimator plates inserted in the grooves toward side walls of the grooves. The collimator plates are inserted into the grooves, then the urging members are slid and held in that slide position to urge individual collimator plates into close contact with side walls of the grooves.

20 Claims, 11 Drawing Sheets

COLLIMATOR UNIT, RADIATION DETECTING DEVICE, AND RADIODIAGNOSTIC SYSTEM

CROSS REFERENCE TO RELATED APPLICATIONS

This application claims the benefit of Japanese Patent Application No. 2009-067200 filed Mar. 19, 2009, which is hereby incorporated by reference in its entirety.

BACKGROUND OF THE INVENTION

The embodiments described herein relate to a collimator unit for removing scattered radiation in a radiation detecting device, as well as a radiation detecting device and a radiodiagnostic system.

An X-ray CT apparatus, which is one example of a radiodiagnostic system, is provided with collimator plates for removing scattered X-rays. Generally, the collimator plates are installed between a pair of holding members. For example, the collimator plates are inserted into grooves formed in mutually opposed surfaces of the pair of holding members and are fixed by bonding (see, for example, Japanese Unexamined Patent Publication No. 2001-174566 and Japanese Unexamined Patent Publication No. 2003-207575).

BRIEF DESCRIPTION OF THE INVENTION

Collimator plates are used for removing, out of X-rays emitted from an X-ray tube, X-rays which have been scattered within a subject so that only X-rays having traveled straight ahead through the interior of the subject are detected by X-ray detecting elements. Therefore, the collimator plates are installed so that their plate surfaces face toward an X-ray focal point. Accordingly, the foregoing grooves are formed so that the collimator plates are installed in such a direction.

Plural collimator plates are provided in a channel direction (a direction orthogonal to the body axis direction of a subject) at a pitch corresponding to the width of each scintillator as an X-ray detecting element. Therefore, the foregoing grooves are formed so that the collimator plates are disposed at such a pitch.

However, since there are variations in thickness of collimator plates and in width of grooves, a gap may be formed between a collimator plate inserted into each of the grooves and a side wall of the groove. If the collimator plate is bonded in the presence of such a gap, the mounting accuracy is deteriorated. If the mounting accuracy is poor, the scattered X-ray removing accuracy is deteriorated; besides, there occur deteriorations of various characteristics such as variations in detectivity of the X-ray detecting device concerned, variations in energy characteristics, and variations in directivity of an X-ray beam. As a result, the quality of an acquired image is deteriorated.

In view of the above-mentioned circumstances the present invention provides a collimator unit, a radiation detecting device, and a radiodiagnostic system, wherein collimator plates can be installed with a high accuracy irrespective of variations in thickness of collimator plates and in width of grooves.

The present invention, in a first aspect thereof, provides a collimator unit in a radiation detecting system, comprising a pair of holding members having a plurality of grooves formed in respective mutually opposed surfaces, collimator plates inserted respectively into the plural grooves formed in the holding members, and an urging member disposed between the pair of holding members, and having engaging portions each adapted to engage a plate surface of each of the inserted collimator plates, the engaging portions each urging the plate surface toward a side wall of the corresponding groove formed in the holding members.

The present invention, in a second aspect thereof, provides the collimator unit of the above first aspect wherein a plurality of notched grooves as the engaging portions are formed in the urging member in substantially the same positional relation as the positional relation of the grooves of the holding members, and each of the collimator plates is held grippingly between a side wall of the corresponding grooves formed in the holding members and a side wall of the corresponding notched groove in the urging member.

The "substantially the same positional relation" means that the grooves of the holding member and the notched grooves of the urging member are positionally close to each other to the extent of the collimator plates being capable of insertion respectively into overlapped grooves when the grooves of the holding member and the notched grooves of the urging member are disposed so as to overlap each other.

The present invention, in a third aspect thereof, provides the collimator unit of the above second aspect wherein the urging member is disposed in abutment against or in proximity to the grooves-formed surface of each of the holding members.

The present invention, in a fourth aspect thereof, provides the collimator unit of the above second or third aspect wherein the urging member has a first plate-like member and a second plate-like member fixed to the first plate-like member, and the plural notched grooves are formed in the second plate-like member.

The present invention, in a fifth aspect thereof, provides the collimator unit of the above fourth aspect, wherein the first plate-like member has rigidity and the second plate-like member has elasticity.

The present invention, in a sixth aspect thereof, provides the collimator unit of the above fifth aspect, wherein the first plate-like member contains as a principal component any of steel, stainless steel, and aluminum alloy, and has a predetermined thickness of not smaller than 0.5 millimeter and not larger than 3 millimeters.

The present invention, in a seventh aspect thereof, provides the collimator unit of the above fifth or sixth aspect wherein the second plate-like member contains as a principal component any of steel, stainless steel, phosphor bronze, copper alloy, and plastic, and has a predetermined thickness of not smaller than 0.1 millimeter and not larger than 0.5 millimeter.

The present invention, in an eighth aspect thereof, provides the collimator unit of any of the above first to seventh aspects wherein the side walls of the grooves in the holding members to which the collimator plates are urged are formed in the direction in which the collimator plates are to be installed.

The present invention, in a ninth aspect thereof, provides the collimator unit of any of the above first to eighth aspects wherein the side walls of the grooves in the holding members to which the collimator plates are urged are formed at a pitch at which the collimator plates are to be installed.

The present invention, in a tenth aspect thereof, provides the collimator unit of any of the above first to ninth aspects wherein in each of the holding members a plurality of grooves are formed in a notched manner along one edge of a plate-like member.

The present invention, in an eleventh aspect thereof, provides the collimator unit of any of the first to ninth aspects wherein in each of the holding members a plurality of grooves are formed on a plate surface of a plate-like member.

The present invention, in a twelfth aspect thereof, provides the collimator unit of any of the above first to eleventh aspects wherein the urging member engages the holding members through a rotating member having an eccentric structure.

The present invention, in a thirteenth aspect thereof, provides the collimator unit of any of the above first to eleventh aspects wherein the urging member engages the holding members through a rotating member having a cam structure.

The present invention, in a fourteenth aspect thereof, provides the collimator unit of any of the above first to thirteenth aspects wherein the collimator plates contain molybdenum or tungsten as a principal component.

The present invention, in a fifteenth aspect thereof, provides the collimator unit of any of the above first to fourteenth aspects wherein at least one of the urging members is disposed for each of the holding members.

The present invention, in a sixteenth aspect thereof, provides a radiation detecting device having the collimator unit of any of the above first to fifteenth aspects.

The present invention, in a seventeenth aspect thereof, provides a radiodiagnostic system having the radiation detecting device of the above sixteenth aspect.

According to embodiments of the present invention, since each collimator plate inserted into the corresponding groove formed in the holding member is urged toward a side wall of the groove of the holding member, it is possible to diminish the gap between the collimator plate and the side wall of the groove of the holding member and hence each collimator plate can be installed with a high accuracy irrespective of variations in thickness of the collimator plate and in width of each groove of the holding member.

DETAILED DESCRIPTION OF THE INVENTION

Embodiments of the present invention will be described below.

First Embodiment

Figure 1:
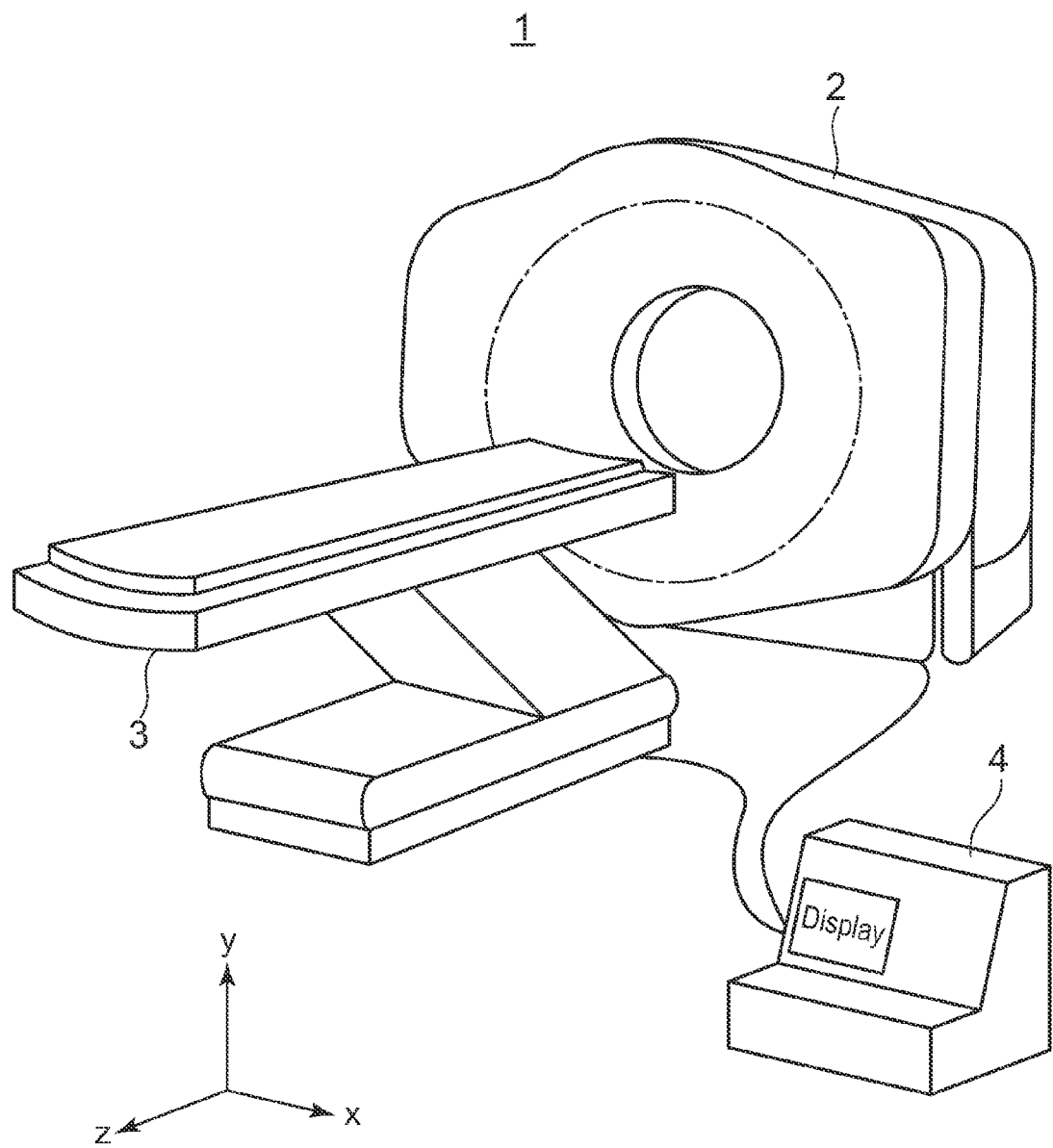
FIG. 1 is a diagram showing an appearance of an X-ray CT apparatus according to a first embodiment.

FIG. 1 is a diagram showing an appearance of an X-ray CT apparatus according to a first embodiment. As shown in FIG. 1, an X-ray CT apparatus 1 includes a scan gantry 2 adapted to scan an object to be scanned and collect projection data, a scan table 3 adapted to move in and out of an opening of the scan gantry as a scanning space while carrying the to-be-scanned object thereon, and an operating console 4 adapted to accept operation of this system and reconstruct an image on the basis of the collected projection data. The scan gantry 2 includes an X-ray tube and an X-ray detecting device for scanning the object to be scanned. The X-ray CT apparatus is an example of the "radiodiagnostic system" defined in the present invention. The X-ray detecting device is an example of the "radiation detecting device" defined in the present invention.

For the convenience of explanation it is here assumed that, as shown in FIG. 1, the movement directions of the object to be scanned by the scan table 3 are z direction, a vertical direction is y direction, and a horizontal direction orthogonal to both y and z directions is x direction.

Figure 2:
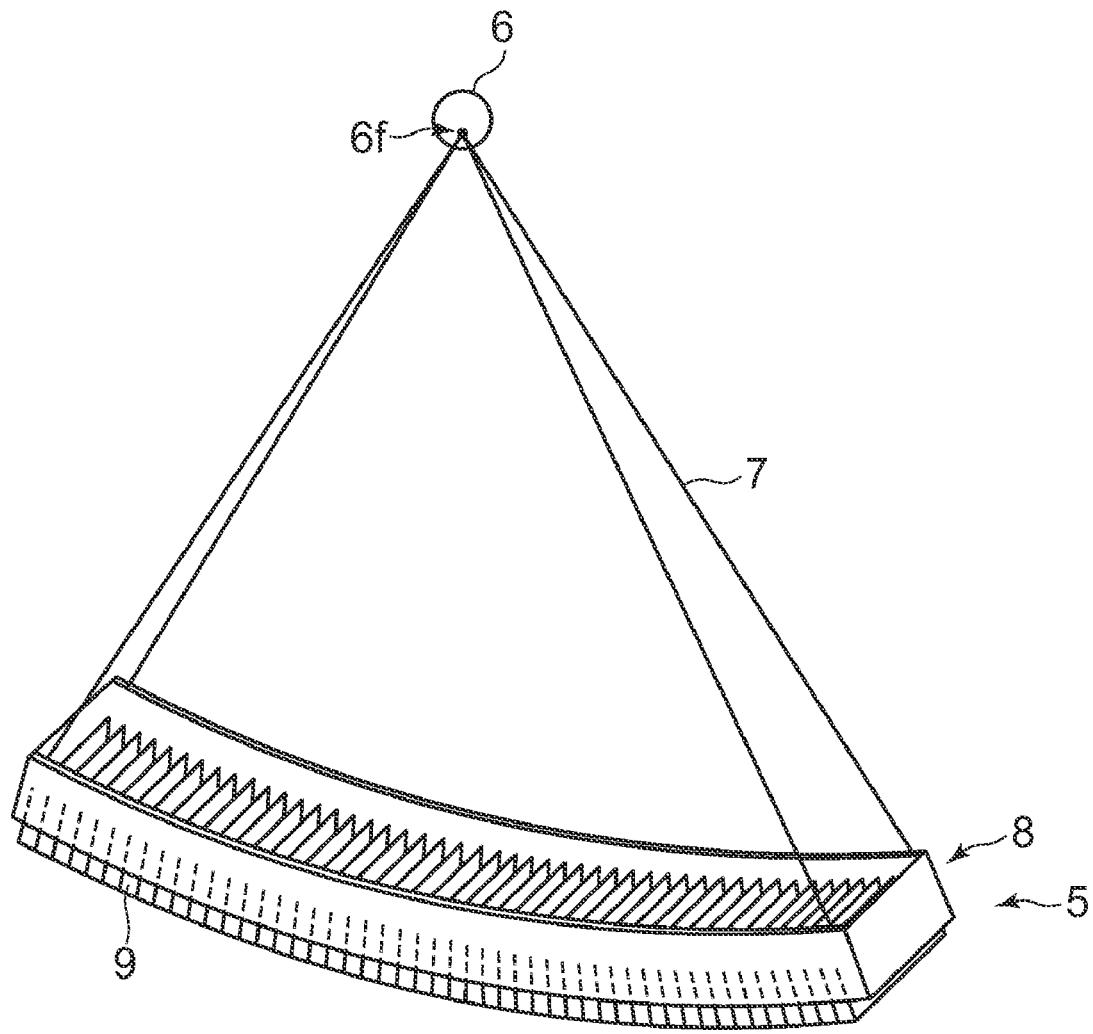
FIG. 2 is a perspective view of an X-ray tube and an X-ray detecting device according to the first embodiment.

FIG. 2 is a perspective view of an X-ray tube and an X-ray detecting device according to the first embodiment.

An X-ray detecting device 5 and an X-ray tube 6 are installed so as to confront each other with the opening of the scan gantry 2 therebetween. An X-ray beam 7 radiated from an X-ray focal point 6f of the X-ray tube 6 is detected by the X-ray detecting device 5. The X-ray detecting device 5 includes a collimator unit 8 and a plurality of detector units 9 which are disposed on the side opposite to the installed side of the X-ray tube 6 with respect to the collimator unit 8. The detector units 9 are each provided with a scintillator (not shown) adapted to emit light upon receipt of X-ray and a photodiode (not shown) adapted to receive the light emitted from the scintillator and generate a signal current.

Figure 3:
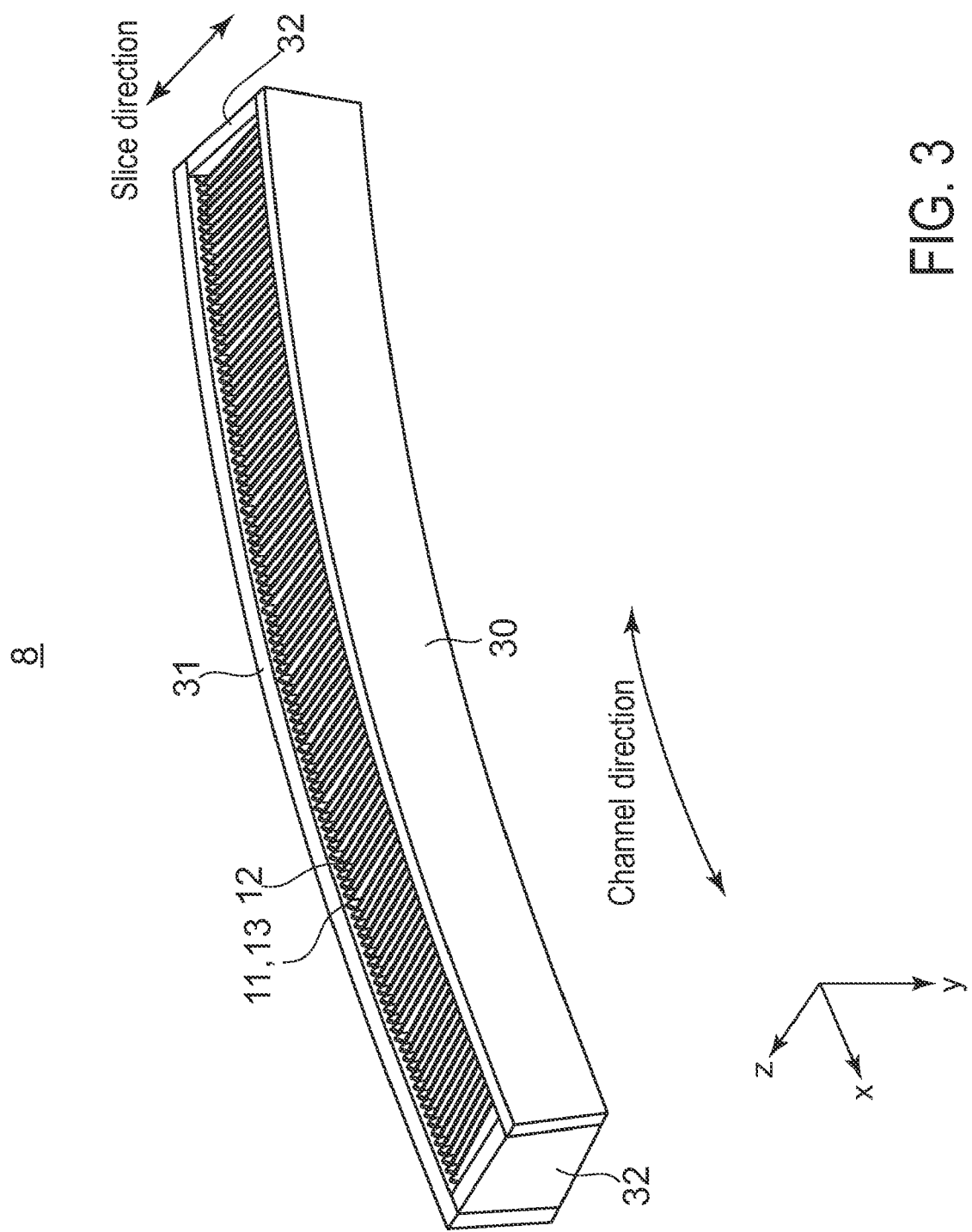
FIG. 3 is an entire perspective view of a collimator unit according to the first embodiment.
Figure 4:
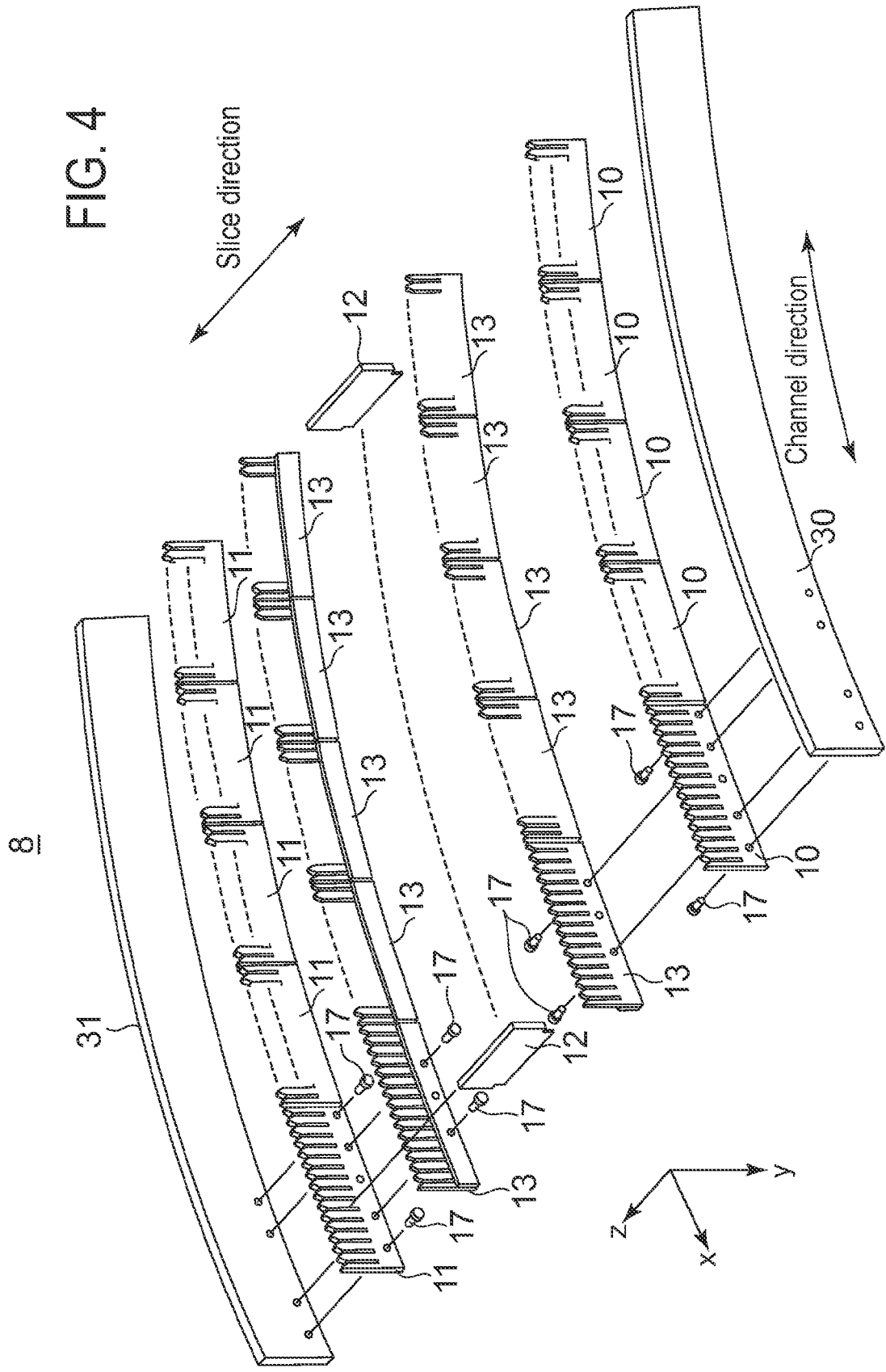
FIG. 4 is a diagram showing schematically an entire construction of the collimator unit according to the first embodiment.

The structure of the collimator unit 8 will now be described in detail. FIG. 3 is an entire perspective view of the collimator unit according to the first embodiment as seen from the disposed side of the detector units. FIG. 4 is a diagram showing schematically an entire construction of the collimator unit according to the first embodiment, FIG. 5 is a partially enlarged construction diagram of the collimator unit according to the first embodiment, and FIG. 6 is a partially enlarged plan view of the collimator unit according to the first embodiment.

As shown in FIGS. 3 and 4, the collimator unit 8 includes a pair of arcuate rails 30 and 31, support struts 32 for fixing the rails 30 and 31 in parallel, holding members 10 and 11 which are arcuate plate-like members formed with plural grooves and which are fixed onto mutually opposed surfaces of the rails 30 and 31 respectively, collimator plates 12 inserted respectively into the plural grooves formed in the holding members 10 and 11, and urging members 13 disposed in abutment against or in proximity to the grooves-formed surfaces of holding members 10 and 11 respectively. The urging members 13 are adapted to urge the individual collimator plates 12 inserted into the grooves of the holding members 10 and 11 toward side walls of the grooves when sliding in the arranged direction of the grooves.

Figure 5:
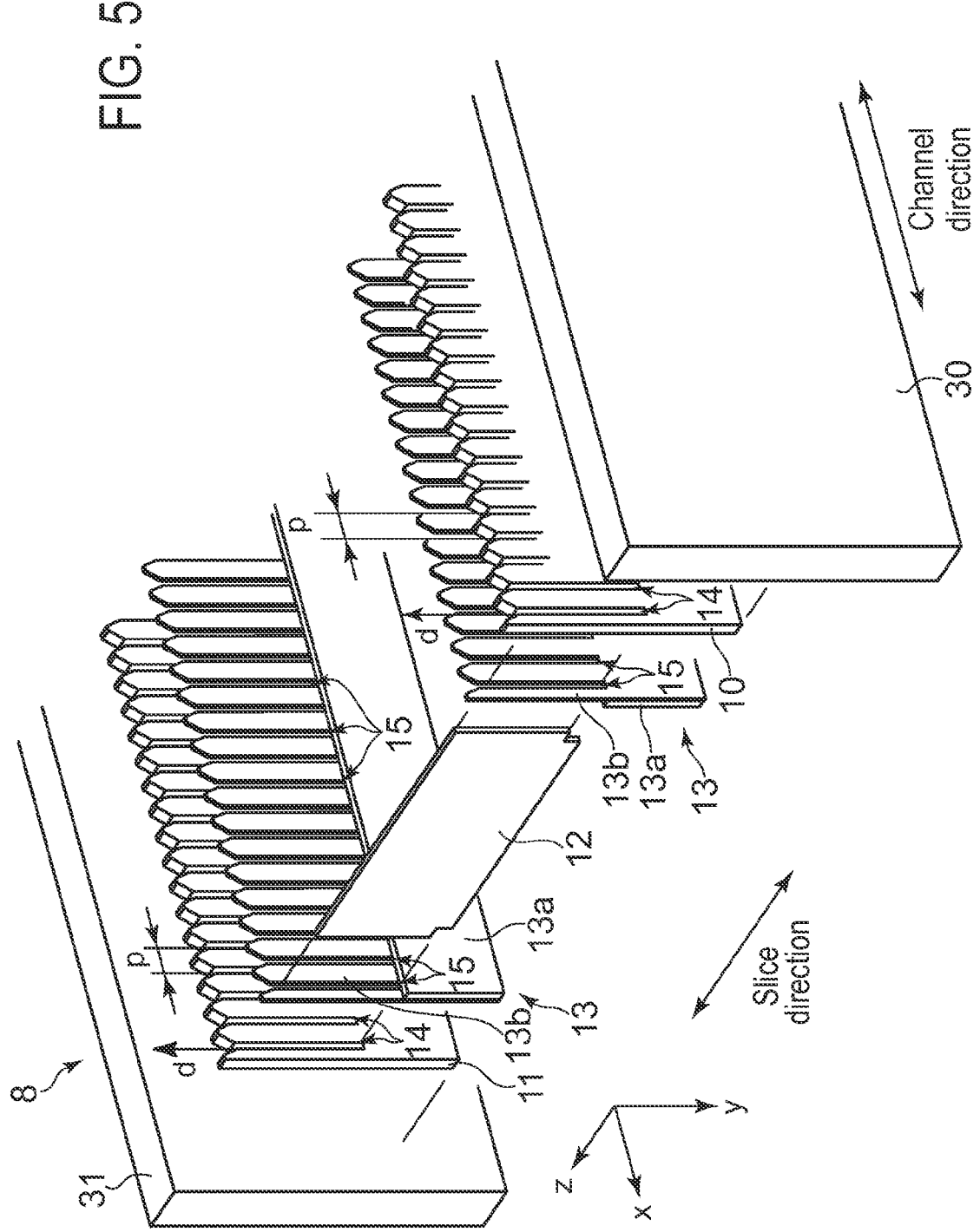
FIG. 5 is a partially enlarged construction diagram of the collimator unit according to the first embodiment.

As shown in FIG. 5, the holding members 10 and 11 are plate-like members and a plurality of grooves 14 are formed along one edge of each of the holding members in a notched manner at a pitch, p. That is, the holding members 10 and 11 have a comb-like shape. The width of each groove 14 may be, for example, 0.1 to 1.5 [mm] though depending on the thickness of each collimator plate 12. Preferably, it is about 1.5 to 3 times the thickness of each collimator plate 12. In this example the width of each groove 14 is about twice the thickness of each collimator plate 12. The holding members 10 and 11 have rigidity and contain, for example, steel, stainless steel, or aluminum alloy, as a principal component. They each have a thickness of 0.5 to 3.0 [mm] In this example, the thickness of each of the holding members 10 and 11 is about 1.0 [mm].

Figure 6:
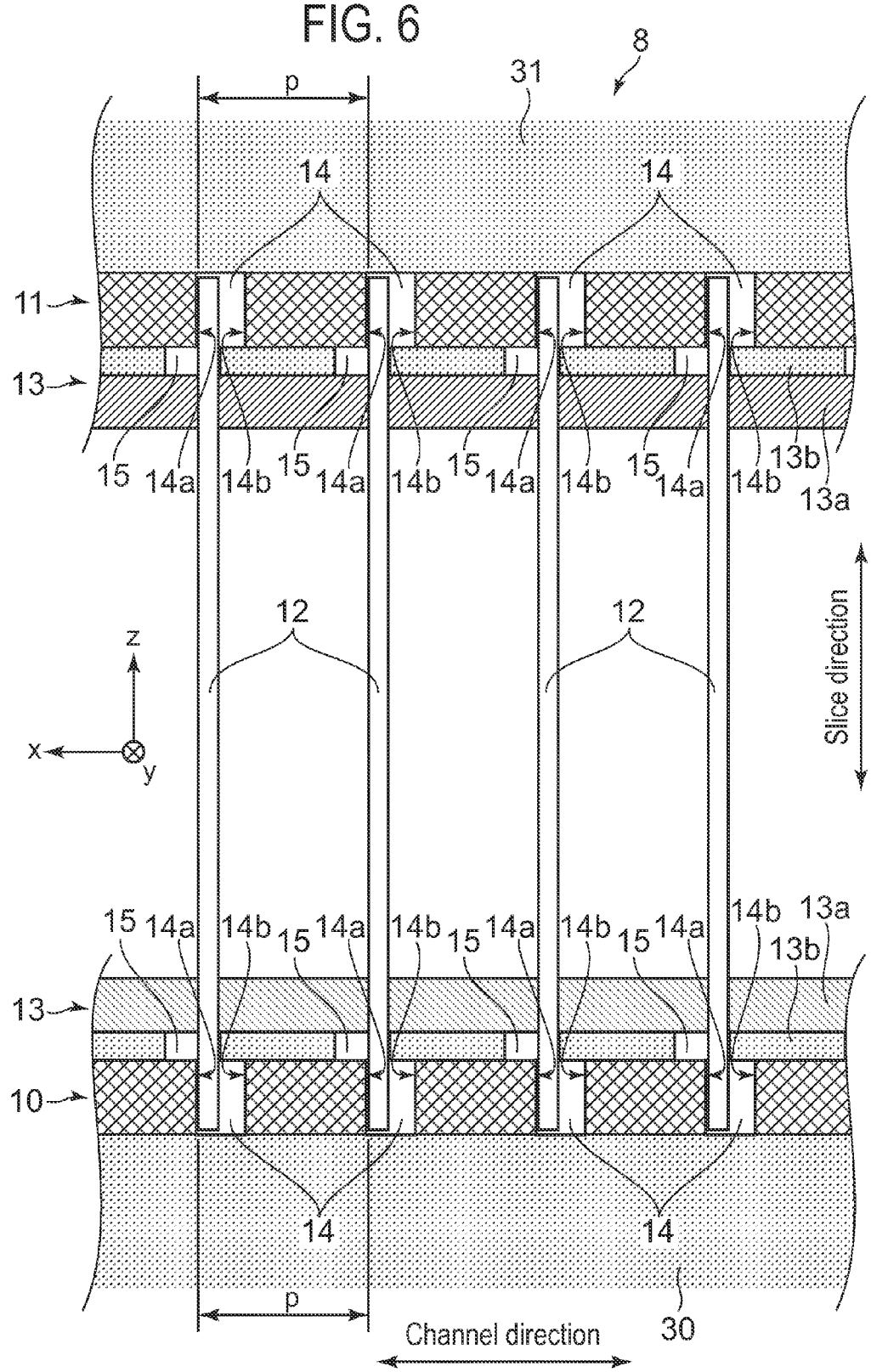
FIG. 6 is a partially enlarged plan view of the collimator unit according to the first embodiment.

As shown in FIGS. 5 and 6, the holding members 10 and 11 are fixed onto mutually confronting surfaces of the rails 30 and 31 respectively. The holding members 10 and 11 are disposed in parallel so that their surfaces formed with the grooves 14 are opposed to each other in a slice direction (the body axis direction of a subject). In this example, as shown in FIG. 4, a plurality of holding members 10 are fixed to the rail 30 adjacently in the arcuate longitudinal direction of the rail 30 and likewise a plurality of holding members 11 are fixed to the rail 31 adjacently in the arcuate longitudinal direction of the rail 31. The holding members 10 and 11 are fixed to the rails 30 and 31 respectively with use of screws 17. The rails 10 and 11 may each be a single plate having a length almost equal to that of the rail 30 (31). The holding members 10 and 11 may be fixed using a combination of both screws 17 and an adhesive or an adhesive alone.

As shown in FIGS. 5 and 6, each of the collimator plates 12 is inserted for each pair of mutually opposed grooves 14 in each pair of holding plates 10 and 11. Thus, plural collimator plates 12 are disposed in the channel direction. The collimator plates 12 are each constructed of an X-ray absorbing material. For example, it contains molybdenum or tungsten as a principal component. The thickness of each collimator plate 12 is in many cases 0.1 to 0.5 [mm] though depending on the size of each detector unit 9 (detecting element). In this example the thickness of each collimator plate 12 is about 0.2 [mm].

As shown in FIG. 4, the urging members 13 are disposed for the holding members 10 and 11 respectively. As shown in FIGS. 5 and 6, the urging members 13 each include an abutting plate portion 13a constituted by an arcuate plate-like member and a spring plate portion 13b constituted by an arcuate plate-like member fixed overlappedly to the abutting plate portion 13a. The abutting plate portion 13a is an example of the "first plate-like member" in the present invention and the spring plate portion 13b is an example of the "second plate-like member" in the present invention.

The abutting plate portion 13a and the spring plate portion 13b are fixed together for example by spot welding or with use of an adhesive. As shown in FIG. 5, a plurality of notched grooves 15 are formed along one edge of the spring plate portion 13b at a predetermined same pitch, p, as that in the holding members 10 and 11. In this example, the spring plate portion 13b is substantially the same shape as the holding members 10 and 11 except the shape in its thickness direction. The width of each notched groove 15 is almost equal to that of each groove 14 in the holding members 10 and 11. The notched groove 15 is also an example of the "engaging portion" in the present invention.

The abutting plate portion 13a has rigidity. The abutting plate portion 13a contains, for example, steel, stainless steel, or aluminum alloy, as a principal component and the thickness thereof is 0.5 to 3.0 [mm]. In this example, the thickness of the abutting plate portion 13a is about 1.0 [mm].

The spring plate portion 13b has elasticity. The spring plate portion 13b contains as a principal portion, for example, steel (for spring), stainless steel (for spring), phosphor bronze (for spring), copper alloy, or plastic, and the thickness thereof is 0.1 to 0.5 [mm]. In this example, the spring plate portion 13b is in the shape of sheet to enhance flexibility and the thickness thereof is about 0.2 [mm].

As shown in FIG. 6, the urging members 13 are disposed so that the plate surfaces of the spring plate portions 13b are abutted against mutually opposed surfaces of the holding members 10 and 11 and so that they can slide in the grooves-arranged direction (channel direction) with respect to the holding members 10 and 11. Each urging member 13 is constructed so as to be slidable from a slide position at which each notched groove 15 in the spring plate portion 13b and each groove 14 of the holding member 10 (11) substantially overlap each other up to a slide position corresponding to a displacement of half or more length of the width of the groove 14. The urging member 13 is constructed so that it can hold its slide position. In this example the length of the urging member 13 in the channel direction is almost equal to the length of the holding member 10 (11) and each of the urging members 13 is disposed for each of the holding members 10 and 11. The urging members 13 may each be made shorter than each of the holding members 10 and 11, and two or more urging members may be disposed for each of the holding members 10 and 11.

A description will now be given about a slide mechanism of each urging member 13. Since the urging members 13 disposed on the holding member 10 side and the urging members 13 disposed on the holding member 11 side are of a symmetric construction with respect to the xy plane, a description will here be given only about the slide mechanism of each of the urging members 13 disposed on the holding member 11 side.

Figure 7:
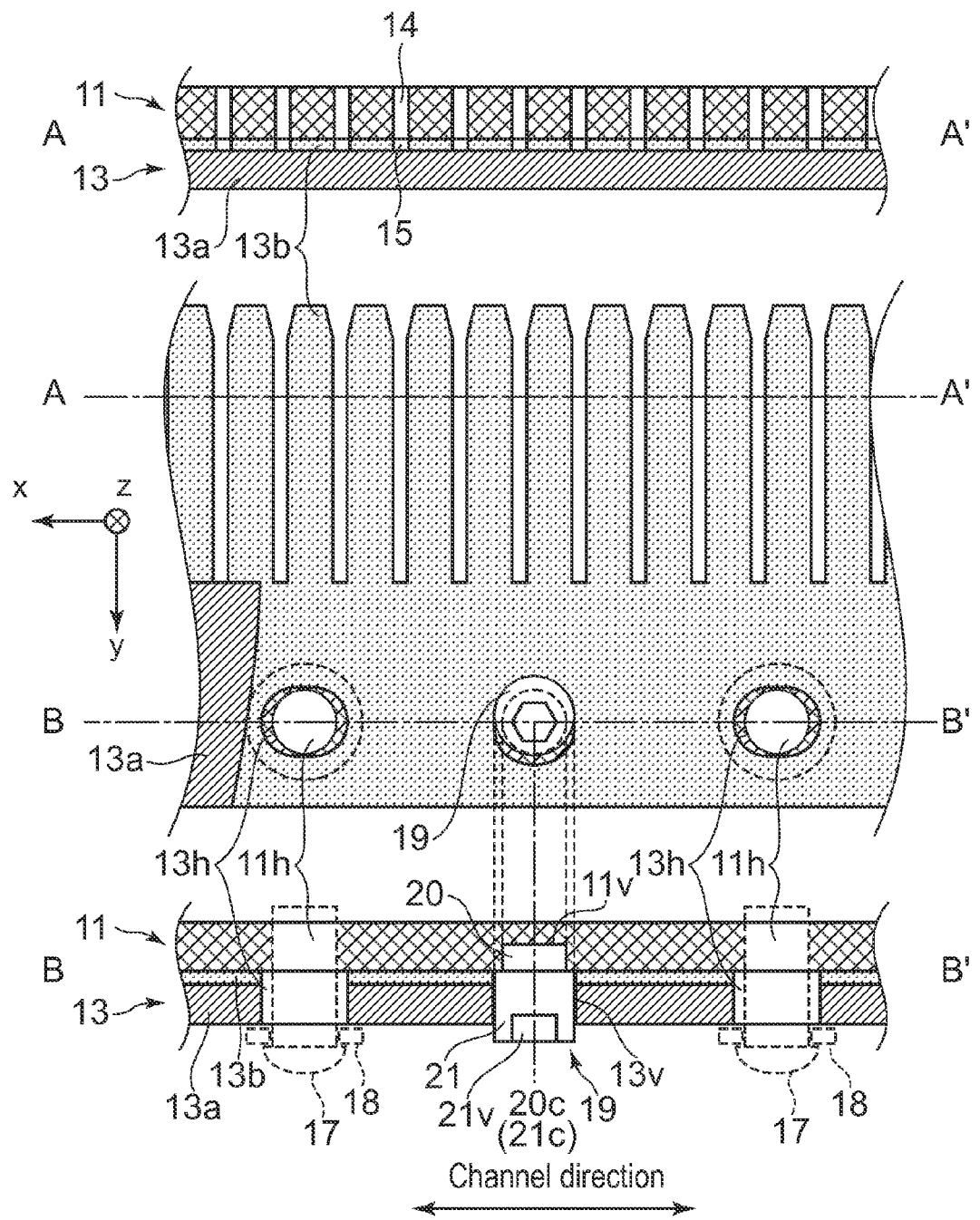
FIG. 7 is a diagram showing a positional relation between a holding member and an urging member before urging collimator plates in the first embodiment.
Figure 8:
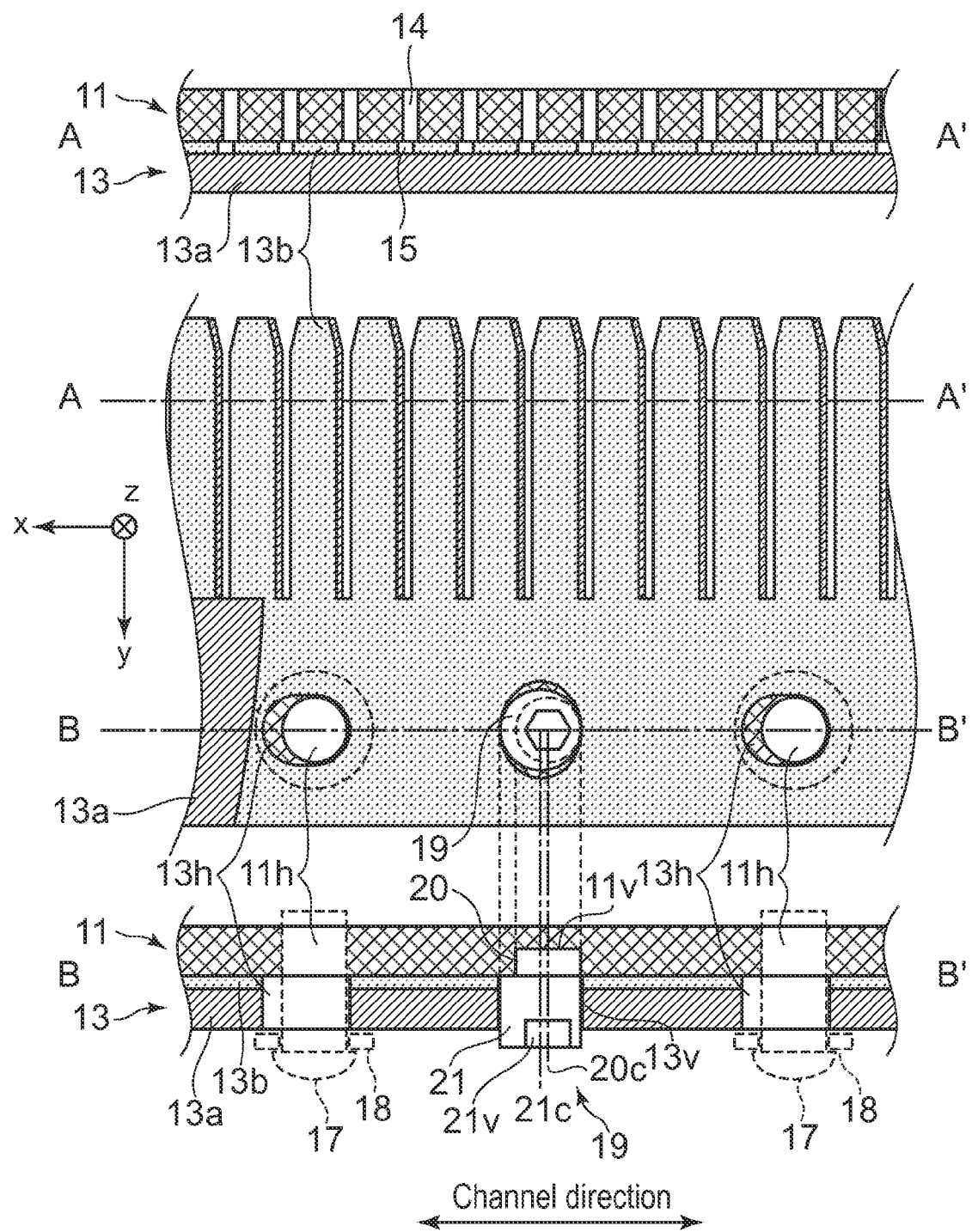
FIG. 8 is a diagram showing a positional relation between the holding member and the urging member after urging the collimator plates in the first embodiment.

FIG. 7 is a diagram showing a positional relation between the holding member and the urging member before urging the collimator plates in the first embodiment. FIG. 8 is a diagram showing a positional relation between the holding member and the urging member after urging the collimator plates in the first embodiment. In FIGS. 7 and 8, the middle stage is a diagram wherein the holding member 11 and the urging member 13 are seen in z direction (slice direction), the upper stage is a sectional view between A and A' of the holding member 11 and the urging member 13 shown in the middle stage, and the lower stage is a sectional diagram between B and B' of the holding member 11 and the urging member 13 shown in the middle stage.

In this example, as shown in FIGS. 7 and 8, tapped holes 11h are formed in plural positions longitudinally of the holding member 11 and laterally long holes 13h, which are laterally longer than the tapped holes 11h, are formed in the urging member 13 at nearly the same positions as the tapped hole positions in the holding member 11. A screw 17 is engaged in each tapped hole 11h of the holding member 11 through a washer 18 and the associated hole 13h of the urging member 13. When the screws 17 are loosened, the urging member 13 becomes slidable, while upon tightening of the screws 17 the urging member 13 is held at that slide position.

In this embodiment, as shown in FIGS. 7 and 8, the urging member 13 and the holding member 11 are constructed so as to engage each other through a rotating member 19 which has an eccentric structure. A columnar recess 11v is formed in a predetermined position of the holding member 11 and a columnar opening 13v is formed in the urging member at a substantially same position as that of the recess 11v. In the rotating member 19, a columnar body 20 fitted in the recess 11v and a columnar body 21 fitted in the opening 13v are fixed in a state in which an axis 20c of the columnar member 20 and an axis 21c of the columnar member 21 are offset from each other by approximately the length equal to the width of the groove 14. The columnar body 21 is formed with a recess 21v for fitting a hexagonal wrench therein. By fitting the rotating member 19 in both recess 11v and opening 13v and then rotating the rotating member 19 with a hexagonal wrench, the urging member 13 can slide in the grooves-arranged direction, i.e., in the channel direction, with respect to the holding member 11.

The slide mechanism of the urging member is not limited to the above example.

Figure 9:
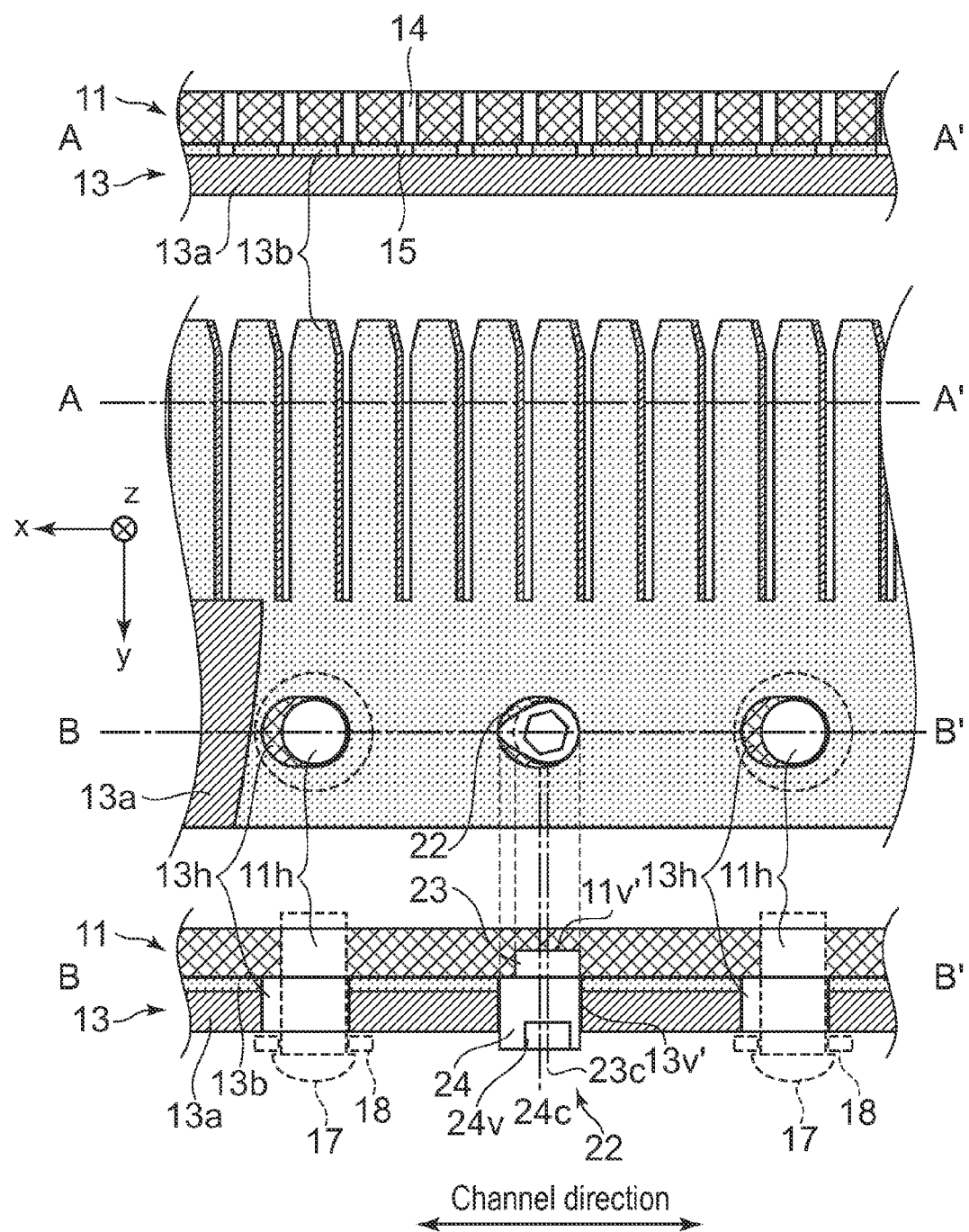
FIG. 9 is a diagram showing another example of a slide mechanism of the urging member.

FIG. 9 is a diagram showing another example of a slide mechanism of the urging member, illustrating a state after urging the collimator plates.

In this another example, as shown in FIG. 9, the urging member 13 and the holding member 11 are constructed so as to engage each other through a rotating member 22 having a cam structure. A columnar recess 11v' is formed in a predetermined position of the holding member 11 and a columnar opening 13v' is formed in the urging member 13 at substantially the same position as the position of the recess 11v'. In the rotating member 22, a columnar body 23 fitted in the recess 11v' and a cam 24 fitted in the opening 13v' are fixed in a state in which a center axis 23c of the columnar body 23 and a rotational axis 24c of the cam 24 are aligned with each other. A longest diameter of the cam 24 is longer than the diameter of the columnar member 23 by a length approximately equal to the width of the groove 14. The cam 24 is formed with a recess 24v for fitting a hexagonal wrench therein. By fitting the rotating member 22 in both recess 11v' and opening 13v' and then rotating the rotating member 22 with a hexagonal wrench, the urging member 13 can slide in the channel direction with respect to the holding member 11.

The rotating members 19 and 22 are not limited to those rotated with a hexagonal wrench. For example, they may be of the type rotated using a plus (+) or minus (−) driver. Alternatively, without using such rotating members, the urging member 13 may be slid in the channel direction by operator's bare hand or by using a suitable tool.

Reference is here made again back to FIGS. 5 and 6. As noted previously, the urging member 13 has the spring plate portion 13b having elasticity. As the urging members 13 are slid in the grooves-arranged direction along the surfaces formed by grooves 14 of the holding members 10 and 11, variations in thickness of the collimator plates 12 and variations in width of the grooves 14 are absorbed by the elasticity of the spring plate portions 13b of the urging members 13, whereby almost all of the collimator plates 12 can be urged against side walls of the grooves 14 in a closely contacted state. In this example, as shown in FIG. 6, each collimator plate 12 is urged into close contact with one side wall 14a out of mutually opposed side walls 14a and 14b of each groove 14. That is, the plate surfaces of the collimator plates 12 are urged in a state in which the side walls of the notched grooves 15 of the spring plate portion 13b are inserted into the grooves 14 of the holding members 10 and 11, causing the collimator plate surfaces to come into close contact with one side walls of the grooves 14.

In this example, the urging member 13 has the abutting plate portion 13a and the spring plate portion 13b, and the spring plate portion 13b is formed in substantially the same shape as the holding members 10 and 11 with use of a material having elasticity such as, for example, stainless steel for spring, provided no limitation is made thereto in the present invention. For example, the spring plate portion 13b may take any shape insofar as it can urge the collimator plates 12 inserted in the grooves 14 against side walls of the same grooves upon sliding of the urging member in the grooves 14-arranged direction. Moreover, the urging member 13 may be a single integral combination of both abutting plate portion 13a and spring plate portion 13b. In this case, the urging member 13 may be constructed of metal such as, for example, stainless steel for spring or non-metal by plastic molding for example. It is preferable that the portion corresponding to the abutting plate portion 13a be made thick to enhance rigidity and the portion corresponding to the spring plate portion 13b be made thin to enhance elasticity.

Further, the urging member 13 may be low in elasticity and high in rigidity. In this case, there may occur a case where the collimator plates 12 cannot be completely brought into close contact with side walls of the grooves 14. However, at least variations in width of the grooves 14 can be absorbed and the gap between each collimator plate 12 and a side wall of a corresponding groove 14 can be kept to a size approximately equal to variations in thickness of the collimator plate 12. Besides, since the grooves 14 of the holding members 10 and 11 can each be designed wide, the machining accuracy for the holding members 10, 11 and the urging member 13 is improved, with the result that the gap between each collimator plate 12 and a side wall of a corresponding groove 14 can be made smaller than in the prior art.

A direction, d, of side wall 14a on one side of each groove 14 extends in a direction which faces the X-ray focal point 6f of the X-ray tube 6, whereby the collimator plate 12 mounted in close contact with the side wall 14a faces in the to-be-installed direction, i.e., in a direction in which the plate surface of the collimator plate 12 faces toward the X-ray focal point 6f of the X-ray tube 6. Each groove 14 is formed radially and each collimator plate 12 is installed radially in each of the holding members 10 and 11.

The pitch, p, of the grooves 14 is set to a pitch corresponding to the width in the scintillator channel direction. In this example, of the opposed side walls 14a and 14b of each groove 14, the side wall for close contact with the collimator plate 12 is the side wall 14a. Thus, the collimator plates 12 are brought into close contact with the side walls located on the same side. Therefore, the pitch, p, of the grooves 14 is set so that the pitch of the collimator plates 12 installed in close contact with the side walls 14a becomes equal to the pitch corresponding to the width in the scintillator channel direction.

Now, a description will be given below about a method for fabricating the collimator unit 8 described above.

First, a pair of rails 30 and 31 are laid in parallel and both end portions in the longitudinal direction of the rails 30 and 31 are fixed with support struts 32. Then, the holding plates 10 and 11 are fixed onto mutually opposed surfaces of the rails 30 and 31. At this time, the fixing of the holding members 10 and 11 is performed in a state in which the grooves 14 formed respectively in the opposed surfaces of the holding members 10 and 11 are aligned with each other.

Then, in a state in which the notched grooves 15 of the urging members 13 are aligned so as to substantially overlap the grooves 14 of the holding members 10 and 11, the urging members 13 are loosely fixed temporarily to the holding members 10 and 11 with use of screws 17.

Next, the collimator plates 12 are inserted into the grooves 14 in the opposed surfaces substantially overlapped with the notched grooves 15. At this time, the collimator plates 12 can be inserted easily because the width of each of the grooves 14 and notched grooves 15 is twice the thickness of each collimator plate 12.

Then, the rotating member 19 is fitted in both recess 11v of the holding member 11 and opening 13v of the urging member 13 and is rotated with use of a hexagon wrench, causing the urging members 13 to slide in the grooves-arranged direction. When all the collimator plates 12 have been urged into close contact with the side walls 14a of the grooves 14, the sliding motion of the urging members 13 is stopped and the screws 17 are tightened strongly to hold that slide position. The same operation is performed also for the other holding members 11 and 10.

Next, the collimator plates 12, the holding members 10, 11 and the urging members 13 are bonded and fixed together with an adhesive or the like, whereby the mounting of the collimator plates 12 is completed.

According to the collimator unit of this example explained above, the individual collimator plates 12 inserted respectively into the grooves formed in the holding members 10 and 11 are urged toward the side walls 14a of the grooves 14 when the urging members 13 slide in the grooves-arranged direction, so that it is possible to diminish the gap formed between each collimator plate 12 and the side wall 14a of the corresponding groove 14 and hence possible to install the collimator plates 12 with a high accuracy irrespective of variations in thickness of the collimator plates 12 and in width of the grooves.

Moreover, since the side walls 14a are formed in the direction facing toward the X-ray focal point 6f of the X-ray tube 6, the collimator plates thus installed in close contact with the side walls 14a can be brought into a state facing in the to-be-installed direction. Besides, since the pitch, p, of the groove side walls 14a is set so that the collimator plates 12 are arranged at a pitch corresponding to the scintillator width, the pitch of the collimator pitch 12 thus installed in close contact with the side walls 14a can be set to a to-be-arranged pitch.

Since the collimator plates 12 are brought into close contact with the side walls 14a by the urging member 13 in the grooves 14, it is not necessary to match the width of each groove 14 with the thickness of each collimator plate 12 and it is possible to make the width of each groove 14 large in comparison with the thickness of each collimator plate 12. Consequently, not only the machinability for the grooves 14 of the holding members 10 and 11 can be improved over the prior art, but also the insertion of the collimator plates 12 into the grooves 14 can be done easily.

Since the holding members 10, 11 and the spring plate portion 13b of the urging member 13 are plate-like, forming of the grooves by for example wire discharge is easy and machining of plural sheets can be done at a time. Thus, the working efficiency is high.

It may be possible to adopt a method which, in order to make the gap as small as possible formed between the collimator plate 12 inserted into each groove 14 and the side wall 14a, involves providing a large number of collimator plates 12 and holding members 10, 11, measuring the width of each collimator plate 12 and the width of each of the grooves 14 formed in the holding members 10, 11, and determining such a collimator plate 12—groove 14 combination as affords a minimum gap. However, such a method requires a complicated work of measuring and recording the thickness of each collimator plate 12 and the width of each groove 14 and looking for an optimum combination. Besides, in order to obtain as optimum a combination as possible it is necessary to have a large stock of collimator plates 12 and holding members 10, 11, which leads to an increase of cost. Moreover, collimator plates 12 and holding members 10, 11 not affording an optimum combination are discarded finally. Further, even if an optimum combination is obtained, it does always lead to a complete elimination of the gap.

On the other hand, according to the construction of this embodiment, it is not necessary to look for an optimum combination because the collimator plate 12 is urged to the side wall 14a of each groove by means of the urging member 13. Consequently, it is neither required to perform a complicated work nor required to have a large stock of the collimator plates 12 and holding members 10, 11. Besides, since there do not occur such collimator plates 12 and holding members 10, 11 as should be discarded in case of an optimum combination being not found out, it is possible to reduce the cost. Further, the gap between the collimator plate 12 and the side wall 14a of each groove can be eliminated almost completely in almost all combinations.

Second Embodiment

Next, a second embodiment of the present invention will be described below.

Figure 10:
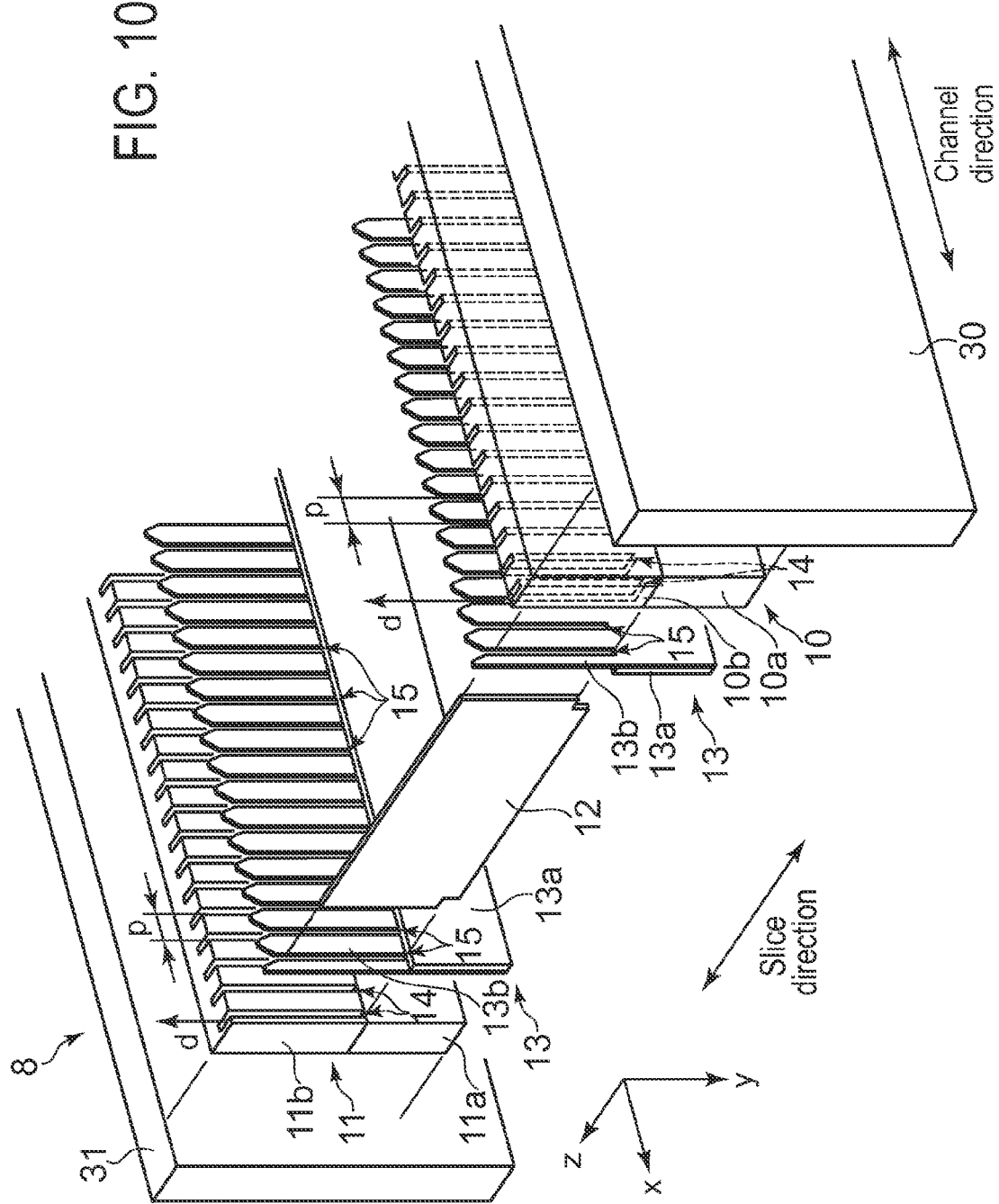
FIG. 10 is a partially enlarged construction diagram of a collimator unit according to a second embodiment.
Figure 11:
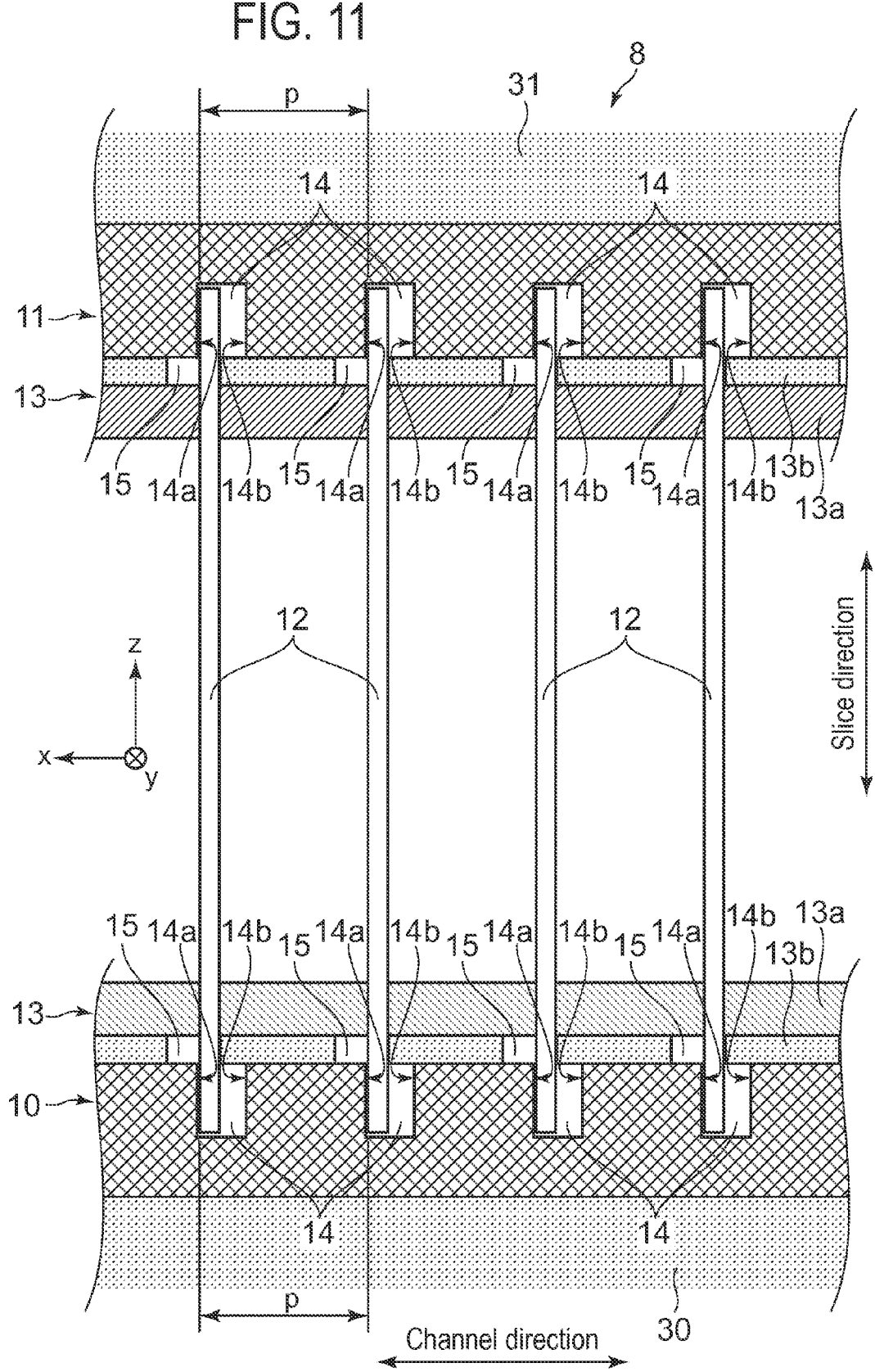
FIG. 11 is a partially enlarged plan view of the collimator unit according to the second embodiment.

FIG. 10 is a partially enlarged construction diagram of a collimator unit of a second embodiment. FIG. 11 is a partially enlarged plan view of the collimator unit of the second embodiment.

In the collimator unit of the second embodiment, grooves 14 are formed not along one edge of an arcuate plate-like member but on a plate surface. In this example, a holding member 10 (11) has a base portion 10a (11a) which is an arcuate plate-like member and a grooves-forming portion 10b (11b) including a plurality of grooves 14 formed on a plate surface of an arcuate plate-like member whose thickness in z direction is approximately equal to that of the base portion. The base portion 10a (11a) and the grooves-forming portion 10b (11b) are fixed in close contact with each other in y direction. The base portion 10a (11a) functions as a stopper in y direction for each of collimator plates 12 inserted into the grooves 14 of the grooves-forming portion 10b (11b). An urging member 13 is constructed so as to engage the base portion 10a (11a) with screws or the like, slide in the grooves-arranged direction and be able to maintain that slide position. The base portion 10a (11a) and the grooves-forming portion 10b (11b) are constructed of, for example, carbon composite, engineering plastic, or aluminum alloy. Other constructional points are the same as in the first embodiment.

Also by the collimator unit of this embodiment described above there can be obtained the same effect as in the first embodiment.

Although the present invention has been described by way of the above embodiments, it goes without saying that the present invention is not limited to those embodiments, but that various modifications may be made within the scope not altering the gist of the invention.

For example, the rail and the holding member may be made integral with each other. Moreover, for example, a collimator unit may be constructed by connecting plural collimator modules each comprising a pair of holding members, urging members each disposed for each holding member, and collimator plates. In these cases, each constituent member can be made small in size and becomes easy to handle. Besides, it becomes easier to determine and maintain a slide position of each urging member.

For example, the material, shape and size of holding members and urging members are not limited to those referred to above.

Further, the present invention is applicable also to other radiodiagnostic systems than the X-ray CT apparatus, such as, for example, PET and SPECT systems.

What is claimed is:

1. A collimator unit in a radiation detecting system, the collimator unit comprising:
    a pair of holding members each comprising a plurality of grooves formed in respective mutually opposed surfaces;
    a plurality of collimator plates inserted respectively into the plurality of grooves formed in each of the pair of holding members; and
    an urging member disposed between the pair of holding members and comprising a plurality of engaging portions each adapted to engage a plate surface of each of the inserted collimator plates, the plurality of engaging portions each adapted to urge the plate surface toward a side wall of a corresponding groove of the plurality of grooves formed in each of the pair of holding members.

2. A collimator unit according to claim 1,
    wherein the plurality of engaging portions comprises a plurality of notched grooves that are formed in the urging member in a position substantially the same as position of the plurality of grooves in each of the pair of holding members, and
    wherein each of the plurality of collimator plates is held grippingly between a side wall of the corresponding groove of the plurality of grooves formed in each of the holding members and a side wall of a corresponding notched groove in the urging member.

3. A collimator unit according to claim 2, wherein the urging member is disposed in abutment against or in proximity to a surface defined by each of the plurality of grooves of each of the pair of holding members.

4. A collimator unit according to claim 2,
    wherein the urging member comprises a first plate-like member and a second plate-like member fixed to the first plate-like member, and
    wherein the plurality of notched grooves is formed in the second plate-like member.

5. A collimator unit according to claim 4, wherein the first plate-like member has rigidity and the second plate-like member has elasticity.

6. A collimator unit according to claim 5, wherein the first plate-like member contains as a principal component any of steel, stainless steel, and aluminum alloy, and has a predetermined thickness of not smaller than 0.5 millimeter and not larger than 3 millimeters.

7. A collimator unit according to claim 5, wherein the second plate-like member contains as a principal component any of steel, stainless steel, phosphor bronze, copper alloy, and plastic, and has a predetermined thickness of not smaller than 0.1 millimeter and not larger than 0.5 millimeter.

8. A collimator unit according to claim 1, wherein the side wall of each of the plurality of grooves in each of the pair of holding members to which the plurality of collimator plates are urged are formed in a direction in which the plurality of collimator plates are to be inserted.

9. A collimator unit according to claim 1, wherein the side wall of each of the plurality of grooves in each of the pair of holding members to which the plurality of collimator plates are urged are formed at a pitch at which the plurality of collimator plates are to be inserted.

10. A collimator unit according to claim 1, wherein each of the pair of holding members comprises a plurality of grooves formed in a notched manner along one edge of a plate-like member.

11. A collimator unit according to claim 1, wherein each of the pair of holding members comprises a plurality of grooves formed on a plate surface of a plate-like member.

12. A collimator unit according to claim 1, wherein the urging member is adapted to engage each of the pair of holding members through a rotating member comprising an eccentric structure.

13. A collimator unit according to claim 1, wherein the urging member is adapted to engage each of the pair of holding members through a rotating member comprising a cam structure.

14. A collimator unit according to claim 1, wherein each of the plurality of collimator plates contain molybdenum or tungsten as a principal component.

15. A collimator unit according to claim 1, wherein the urging member comprises a plurality of urging members, at least one of the plurality of urging members is disposed for each of the pair of holding members.

16. A radiation detecting device comprising:
    a detector unit; and
    a collimator unit coupled to the detector unit, the collimator unit comprising:
        a pair of holding members each comprising a plurality of grooves formed in respective mutually opposed surfaces;
        a plurality of collimator plates inserted respectively into the plurality of grooves formed in each of the pair of holding members; and
        an urging member disposed between the pair of holding members and comprising a plurality of engaging portions each adapted to engage a plate surface of each of the inserted collimator plates, the plurality of engaging portions each adapted to urge the plate surface toward a side wall of a corresponding groove of the plurality of grooves formed in each of the pair of holding members.

17. A radiation detection device according to claim 16,
    wherein the plurality of engaging portions comprises a plurality of notched grooves that are formed in the urging member in a position substantially the same as position of the plurality of grooves in each of the pair of holding members, and
    wherein each of the plurality of collimator plates is held grippingly between a side wall of the corresponding groove of the plurality of grooves formed in each of the holding members and a side wall of a corresponding notched groove in the urging member.

18. A radiation detection device according to claim 17, wherein the urging member is disposed in abutment against or in proximity to a surface defined by each of the plurality of grooves of each of the pair of holding members.

19. A radiodiagnostic system comprising:

a scanning gantry comprising a radiation irradiation device; and a radiation detecting device comprising a collimator unit, said collimator unit comprising:

- a pair of holding members each comprising a plurality of grooves formed in respective mutually opposed surfaces;
- a plurality of collimator plates inserted respectively into the plurality of grooves formed in each of the pair of holding members; and
- an urging member disposed between the pair of holding members and comprising a plurality of engaging portions each adapted to engage a plate surface of each of the inserted collimator plates, the plurality of engaging portions each adapted to urge the plate surface toward a side wall of a corresponding groove of the plurality of grooves formed in each of the pair of holding members.

20. A radiodiagnostic system according to claim 19, wherein the plurality of engaging portions comprises a plurality of notched grooves that are formed in the urging member in a position substantially the same as position of the plurality of grooves in each of the pair of holding members, wherein each of the plurality of collimator plates is held grippingly between a side wall of the corresponding groove of the plurality of grooves formed in each of the holding members and a side wall of a corresponding notched groove in the urging member, and wherein the urging member is disposed in abutment against or in proximity to a surface defined by each of the plurality of grooves of each of the pair of holding members.

* * * * *